US00PP36273P2

(12) United States Plant Patent
van Dijk

(10) Patent No.: US PP36,273 P2
(45) Date of Patent: Nov. 26, 2024

(54) ***ANTHURIUM* PLANT NAMED 'AN2865200'**

(50) Latin Name: *Anthurium andreanum*
Varietal Denomination: AN2865200

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/610,255

(22) Filed: Mar. 19, 2024

(51) Int. Cl.
*A01H 5/02* (2018.01)
*A01H 6/10* (2018.01)

(52) U.S. Cl.
USPC ..... Plt./365

(58) Field of Classification Search
USPC ..... Plt./263.1, 365
See application file for complete search history.

(56) References Cited

U.S. PATENT DOCUMENTS

PP20,676 P2 * 1/2010 van der Knaap ..... Plt./365

* cited by examiner

*Primary Examiner* — Karen M Redden
(74) *Attorney, Agent, or Firm* — C. Anne Whealy

(57) ABSTRACT

A new and distinct cultivar of *Anthurium* plant named 'AN2865200', characterized by its upright to outwardly arching and uniform plant habit; freely clumping growth habit; bushy and dense plants; narrowly cordate dark green-colored leaves; freely flowering habit; inflorescences that are positioned within to slightly above the foliar plane on strong and erect scapes; orbicular cordate purplish red-colored spathes and darker purplish red-colored spadices; and durable spathes that impart good inflorescence longevity.

2 Drawing Sheets

Figure 1:
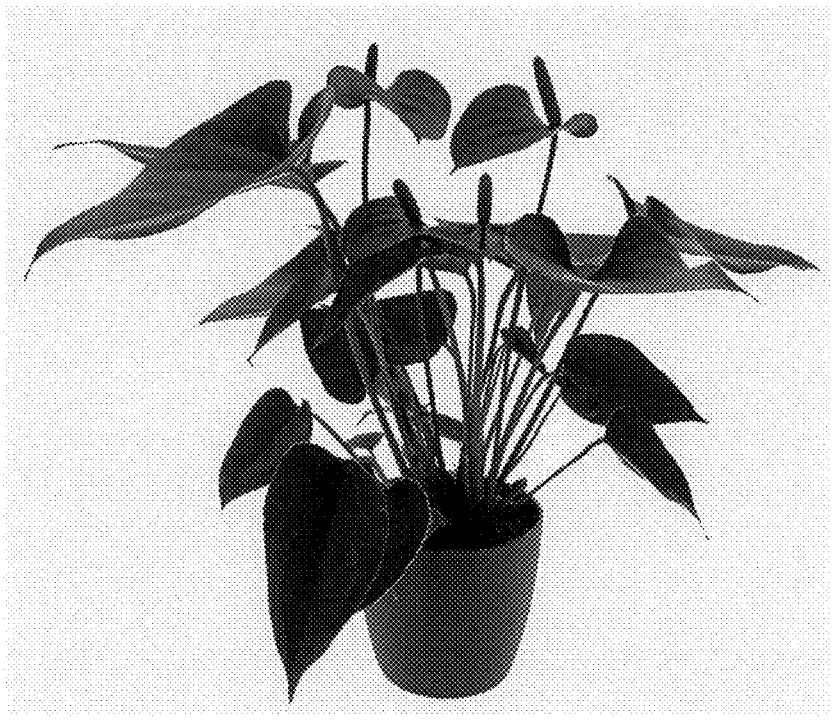

Botanical designation: *Anthurium andreanum.*
Cultivar denomination: 'AN2865200'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B. V. of Bleiswijk, The Netherlands on Nov. 22, 2022, application number 2022/2626. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Anthurium* plant, botanically known as *Anthurium andreanum* and hereinafter referred to by the name 'AN2865200'.

The new *Anthurium* plant is a product of a controlled breeding program conducted by the Inventor in Bleiswijk, The Netherlands. The objective of the breeding program is to create new freely-clumping *Anthurium* plants with attractive purplish red-colored, durable and glossy spathes.

The new *Anthurium* plant originated from a cross-pollination made by the Inventor in September 2015 in Bleiswijk, The Netherlands of a proprietary selection of *Anthurium andreanum* identified as code number 13-034065-0001, not patented, as the female, or seed, parent with a proprietary selection of *Anthurium andreanum* identified as code number 12-028967-001, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in May 2017.

Asexual reproduction of the new *Anthurium* plant by in vitro meristem propagation in a controlled environment in Bleiswijk, The Netherlands since November 2018 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2865200'. These characteristics in combination distinguish 'AN2865200' as a new and distinct *Anthurium* plant:

1. Upright to outwardly arching and uniform plant habit.
2. Freely clumping growth habit; bushy and dense plants.
3. Narrowly cordate dark green-colored leaves.
4. Freely flowering habit.

5. Inflorescences that are positioned within to slightly above the foliar plane on strong and erect scapes.
6. Orbicular cordate purplish red-colored spathes and darker purplish red-colored spadices.
7. Durable spathes that impart good inflorescence longevity.

Plants of the new *Anthurium* differ primarily from plants of the female parent selection in the following characteristics:

1. Spathes of plants of the new *Anthurium* are orbicular cordate in shape whereas spathes of plants of the female parent selection are ovate.
2. Spathes of plants of the new *Anthurium* are not as concave as spathes of plants of the female parent selection.

Plants of the new *Anthurium* differ primarily from plants of the male parent selection in the following characteristics:

1. Spathes of plants of the new *Anthurium* are smaller than spathes of plants of the male parent selection.
2. Spathes of plants of the new *Anthurium* are not as rugose as spathes of plants of the male parent selection.
3. Spadices of plants of the new *Anthurium* are dark purplish red in color whereas spadices of plants of the male parent selection are white and yellow in color.

Plants of the new *Anthurium* can also be compared to plants of *Anthurium andreanum* 'Anthdubaq', disclosed in U.S. Plant Pat. No. 27,889. In side-by-side comparisons, plants of the new *Anthurium* differ primarily from plants of 'Anthdubaq' in the following characteristics:

1. Spathes of plants of the new *Anthurium* are positioned lower in relation to the foliar plane than spathes of plants of 'Anthdubaq'.
2. Spadices of plants of the new *Anthurium* are straighter than spadices of plants of 'Anthdubaq'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2865200' grown in a container.

Figure 2:
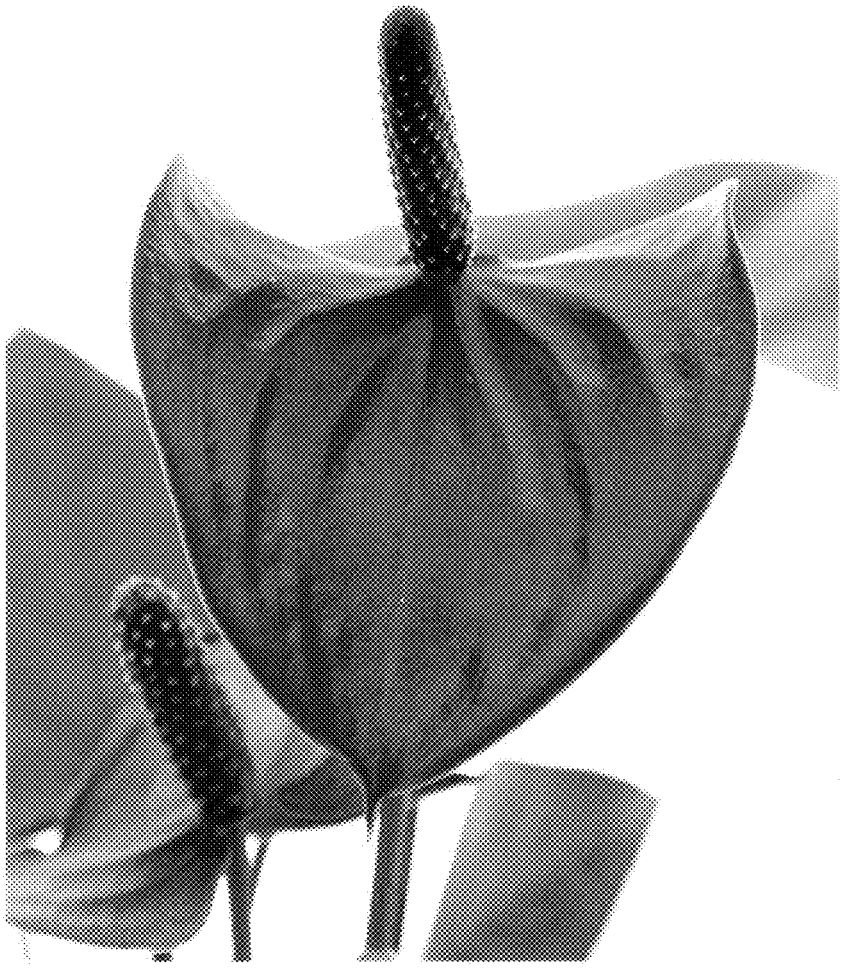

The photograph on the second sheet (FIG. 2) is a close-up view of typical inflorescences of 'AN2865200'.

DETAILED BOTANICAL DESCRIPTION

The aforementioned photographs and following observations and measurements describe plants grown in 9-cm containers in Bleiswijk, The Netherlands during the autumn in a glass-covered greenhouse. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were nine months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2865200'.

Parentage:

*Female, or seed, parent*.—Proprietary selection of *Anthurium andreanum* identified as code number 13-034065-0001, not patented.

*Male, or pollen, parent*.—Proprietary selection of *Anthurium andreanum* identified as code number 12-028967-0001, not patented.

Propagation:

*Type*.—By in vitro meristem propagation.

*Time to initiate roots, summer and winter*.—About two weeks at temperatures about 19° C. to 22.5° C.

*Time to produce a rooted young plant, summer and winter*.—About six to eight weeks at temperatures about 19° C. to 22.5° C.

*Root description*.—Medium in thickness, fibrous; typically creamy white slightly tinged with pink in color, actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly spreading and uniform plant habit; overall shape, broadly obovate.

*Growth habit*.—Freely clumping habit with about six clumps per plant imparting a bushy and dense appearance; moderately vigorous growth habit and moderate growth rate.

*Plant height, from soil level to top of leaf plane*.—About 23.2 cm.

*Plant height, from soil level to top of inflorescences*.—About 25.5 cm.

*Plant diameter or spread*.—About 34.5 cm.

Leaf description:

*Arrangement*.—Alternate; simple; about three leaves per clump.

*Length*.—About 14.7 cm.

*Width*.—About 8.7 cm.

*Shape*.—Narrowly cordate.

*Apex*.—Apiculate with mucronate tip.

*Base*.—Cordate.

*Margin*.—Entire; slightly and coarsely undulate.

*Texture and luster, upper and lower surfaces*.—Smooth, glabrous; moderately leathery; glossy.

*Venation pattern*.—Pinnate.

*Color*.—Developing leaves, upper surface: Darker than a blend of 143A and 146A. Developing leaves, lower surface: Close to a blend of 146B and 147B. Fully expanded leaves, upper surface: Slightly darker than a blend of NN137A and N189A; venation, close to 143B. Fully expanded leaves, lower surface: Close to a blend of 144A and 146B; venation, close to N144C.

*Petioles*.—Length: About 16.9 cm. Diameter: Distally, about 3 mm; proximally, about 4 mm. Strength: Strong. Texture and luster, upper and lower surfaces: Smooth, glabrous; moderately glossy. Color, upper surface: Distally, close to 144A and proximally, close to 144B. Color, lower surface: Close to 146C. Geniculum length: About 2.2 cm. Geniculum diameter: About 3.5 mm. Geniculum texture and luster, upper and lower surfaces: Smooth, glabrous; moderately glossy. Geniculum color, upper surface: Close to 146B; occasionally tinged with close to 177A. Geniculum color, lower surface: Close to 146C and 146D; towards the base, occasionally slightly tinged with close to 177A. Wing length: About 2 cm. Wing diameter: About 4.5 mm. Wing color: Close to 153C; towards the base, close to 174B and 174C.

Inflorescence description:

*Inflorescence arrangement and flowering habit.*—Spathes with spadices held within and slightly above the foliar plane on strong and erect scapes; flowering structures arise from leaf axils; freely and continuous flowering year-round in controlled temperature greenhouses in The Netherlands; typically about nine developing and developed inflorescences per plant at one time; inflorescence development commences about 2.5 to 3.5 months after planting.

*Inflorescence longevity.*—Spathes maintain good substance for about two months on the plant; inflorescences persistent.

*Fragrance.*—None detected.

*Spathes.*—Length: About 6.7 cm. Width: About 6.4 cm. Shape: Orbicular cordate; moderately concave to carinate. Apex: Abruptly acute with a mucronate tip. Base: Reniform to shallowly cordate. Margin: Entire; coarsely undulate; involute. Aspect: At about 115° from the peduncle axis. Texture and luster, upper and lower surfaces: Smooth, glabrous; moderately leathery; glossy. Color: When developing, front surface: Close to N79C; towards the margins and apex, closer to a blend of N79B and N79C; narrow marginal edges, close to N79A. When developing, rear surface: Close to a blend of 77A and N79C; towards the base, tinged with close to 146C and 146D; tip, close to 151B; narrow marginal edges, close to N79A. Fully developed, front surface: Close to 61A; towards the base, tinged with close to 146B; tip, close to 150A; narrow marginal edges, close to a blend of 71A and N79B; with subsequent development, color becoming closer to 182A, towards the base, closer to 146B and 146C with venation, close to 200B and 200C and narrow marginal edges, closer to 187B. Fully developed, rear surface: Close to N77B; towards the base, close to a blend of 138B and 144B; tip, close to 150A; narrow marginal edges, close to N79B; with subsequent development, color becoming closer to 148C, towards the center and apex, tinged with closer to N79B with venation, close to 147A and narrow marginal edges, closer to N79B.

*Spadices.*—Length: About 3.3 cm. Diameter: About 8 mm. Shape: Columnar, slightly tapering towards the apex; apex, obtuse; base, obtuse; in cross-section, rounded. Aspect: About 100° from the spathe axis and about 25° from the peduncle axis. Color: Immature: Close to N186C and distally, close to 164A. Mature: Close to N79B and distally, close to N79A; with subsequent development, color becoming closer to 178A. Flowers: Type: Hermaphroditic. Quantity per spadix: Numerous, about 180. Height: Less than 0.5 mm. Diameter: About 2 mm. Shape: Roughly square. Anthers: To date, anther development has not been observed on plants of the new *Anthurium*. Stigma color: Close to 85C to 85D.

*Scape.*—Length: About 20.1 cm. Diameter: About 3.5 mm. Strength: Strong. Aspect: About 15° from vertical. Color: Close to 146C and 146D; distally, strongly tinged with close to 183A.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2865200' as illustrated and described.

* * * * *